US006810879B1

(12) United States Patent
Tinsley

(10) Patent No.: US 6,810,879 B1
(45) Date of Patent: Nov. 2, 2004

(54) LATERAL EPIDURAL POSITIONING DEVICE

(76) Inventor: Ronald E. Tinsley, 2944 Adams St., Eugene, OR (US) 97405

( * ) Notice: Subject to any disclaimer, the term of this patent is extended or adjusted under 35 U.S.C. 154(b) by 0 days.

(21) Appl. No.: 10/447,362

(22) Filed: May 28, 2003

Related U.S. Application Data

(60) Provisional application No. 60/385,180, filed on May 31, 2002.

(51) Int. Cl.[7] ............................................. A61F 13/00
(52) U.S. Cl. .............................. 128/846; 602/4; 602/24
(58) Field of Search ................................ 128/845, 846; 602/4, 24

(56) References Cited

U.S. PATENT DOCUMENTS 3,834,376 A * 9/1974 Thum .......................... 602/24
3,869,021 A * 3/1975 Sutherland et al. ............ 182/3
4,203,433 A * 5/1980 Prahl ............................ 602/24
4,607,629 A * 8/1986 Lerman ........................ 602/24

* cited by examiner

Primary Examiner—Michael A. Brown
(74) Attorney, Agent, or Firm—Robert E. Howard

(57) ABSTRACT

A positioning device for a patient undergoing a lateral epidural procedure. The positioning device includes a shoulder harness subassembly and a leg saddle subassembly. The shoulder harness subassembly is adapted to fit over the shoulders of the patient, and includes a chest strap extending downwardly from the front thereof. The leg saddle subassembly is adapted to fit behind the upper right and left legs of the patient, the saddle subassembly having a saddle strap extending upwardly therefrom. An adjustable strap attachment means is attached to one of the lower end of the chest strap or the upper end of the saddle strap. The adjustable strap attachment means is adapted to adjustably receive the other strap and hold the other strap at a location that restrains the patient in the desired fetal position.

1 Claim, 2 Drawing Sheets

LATERAL EPIDURAL POSITIONING DEVICE

CROSS-REFERENCE TO RELATED APPLICATIONS

This application claims the benefit of U.S. Provisional Application No. 60/385,180, filed May 31, 2002.

BACKGROUND OF THE INVENTION

This invention relates to a device for laterally positioning a patient during an epidural procedure.

Epidural anesthesia or analgesia is one of the most widely used regional anesthetic procedures employed for surgery, obstetrics, postoperative analgesia, and chronic back pain management. In such epidural procedures, anesthetic or analgesic drugs are delivered to the spinal cord by placing the drugs outside of the membranous sac containing the spinal cord using a syringe.

In a lateral epidural procedure the patient lays on their side on an operating or examination table in the fetal position, i.e., with the knees drawn up toward the chest.

It is often difficult for the patient to remain in the fetal position without movement for the period of time required for the procedure. It is obviously very important that the patient does not move during the procedure as such movement could have adverse consequences.

It is an object of the present invention to provide a device for positioning and immobilizing a patient for a lateral epidural procedure.

SUMMARY OF THE INVENTION

The positioning device of the present invention includes a shoulder harness subassembly and a leg saddle subassembly.

The shoulder harness subassembly is adapted to fit over the shoulders of the patient, and includes a chest strap extending downwardly from the front thereof.

The leg saddle subassembly is adapted to fit behind the legs of the patient above the knees, the saddle subassembly having a saddle strap extending upwardly therefrom.

An adjustable strap attachment means is attached to one of the lower end of the chest strap or the upper end of the saddle strap. The adjustable strap attachment means is adapted to adjustably receive the other strap and hold the other strap at a location that restrains the patient in the desired fetal position.

DESCRIPTION OF PREFERRED EMBODIMENTS

The epidural positioning device 10 includes a shoulder harness subassembly 20 and a leg saddle subassembly 30.

Figure 3:
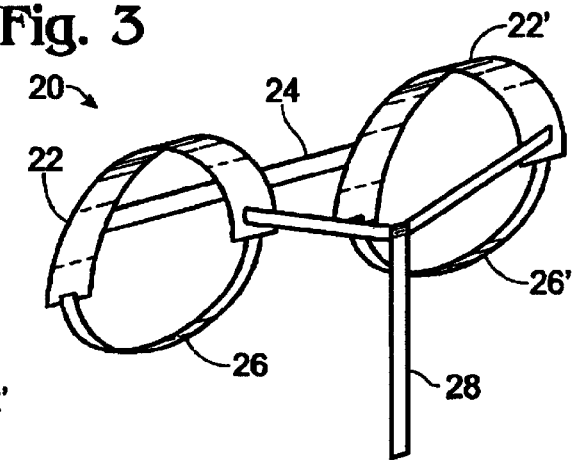
FIG. 3 is a right front perspective view of the shoulder harness subassembly of the epidural positioning device of the present invention.

As best seen in FIG. 3, shoulder harness subassembly 20 includes right and left flexible or rigid shoulder hangers 22 and 22', respectively. Shoulder hangers 22 and 22' are spaced apart and fastened together by a flexible or rigid rear cross member 24. Optional right and left flexible arm straps 26 and 26' are attached at their rear outer ends to the right and left shoulder hangers 22 and 22', respectively, adjacent their rear ends. Right and left arm straps 26 and 26' pass through openings in right and left shoulder hangers 22 and 22', respectively, adjacent their front ends. Right and left arm straps 26 and 26' merge and are joined together with a flexible vertical breast strap 28.

Figure 4:
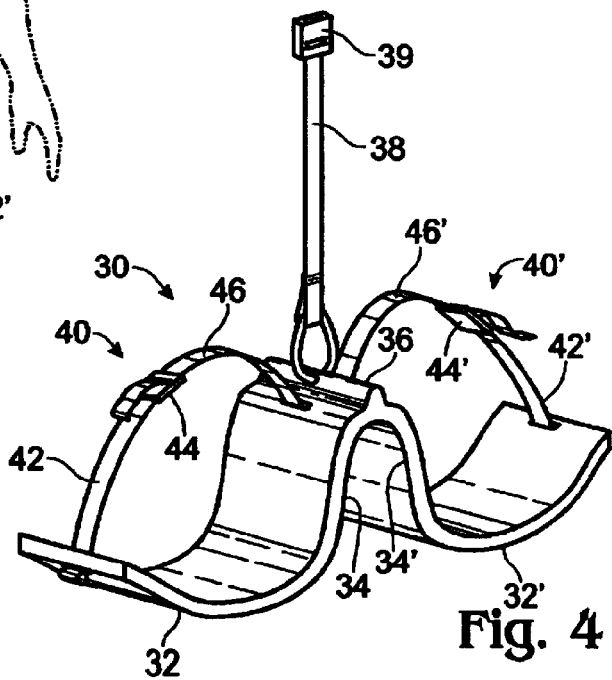
FIG. 4 is a right front perspective view of the leg saddle subassembly of the epidural positioning device of the present invention.

As best seen in FIG. 4, leg saddle subassembly 30 is a rigid or flexible generally inverted U-shaped member that includes right and left upper leg stirrup portions 32 and 32', respectively. Inner leg members 34 and 34' extend vertically upward from leg stirrup portions 32 and 32', respectively, and merge at apex 36. Strap member 38 extends through a centrally located opening in apex 36 and its lower outer end merged with and attached thereto, as shown. A buckle 39 is attached to the upper outer end of strap member 38.

Leg saddle subassembly 30 may, optionally, include right and left flexible and adjustable leg straps 40 and 40', respectively, as seen in FIG. 4. Right and left leg straps 40 and 40' include lower strap members 42, 42' having buckles 44, 44' attached to the outer ends thereof, and upper strap members 46, 46' which are adjustable received through buckles 44, 44', respectively.

Figure 1:
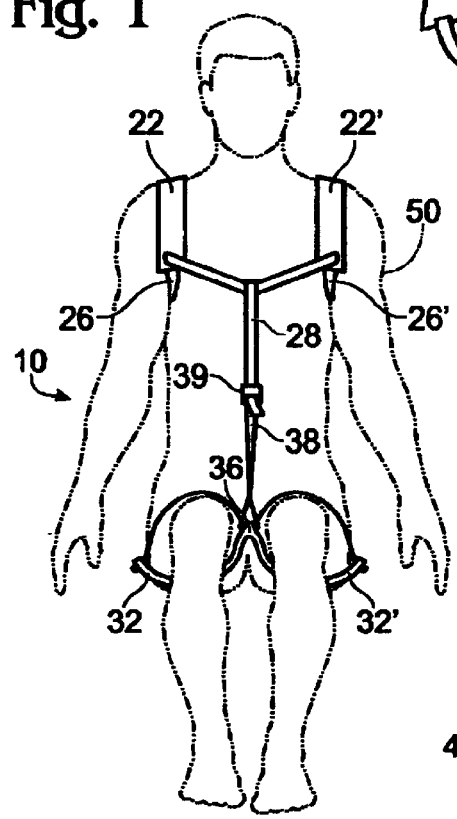
FIG. 1 is a front view of the epidural positioning device of the present invention in place on a patient shown in phantom.
Figure 2:
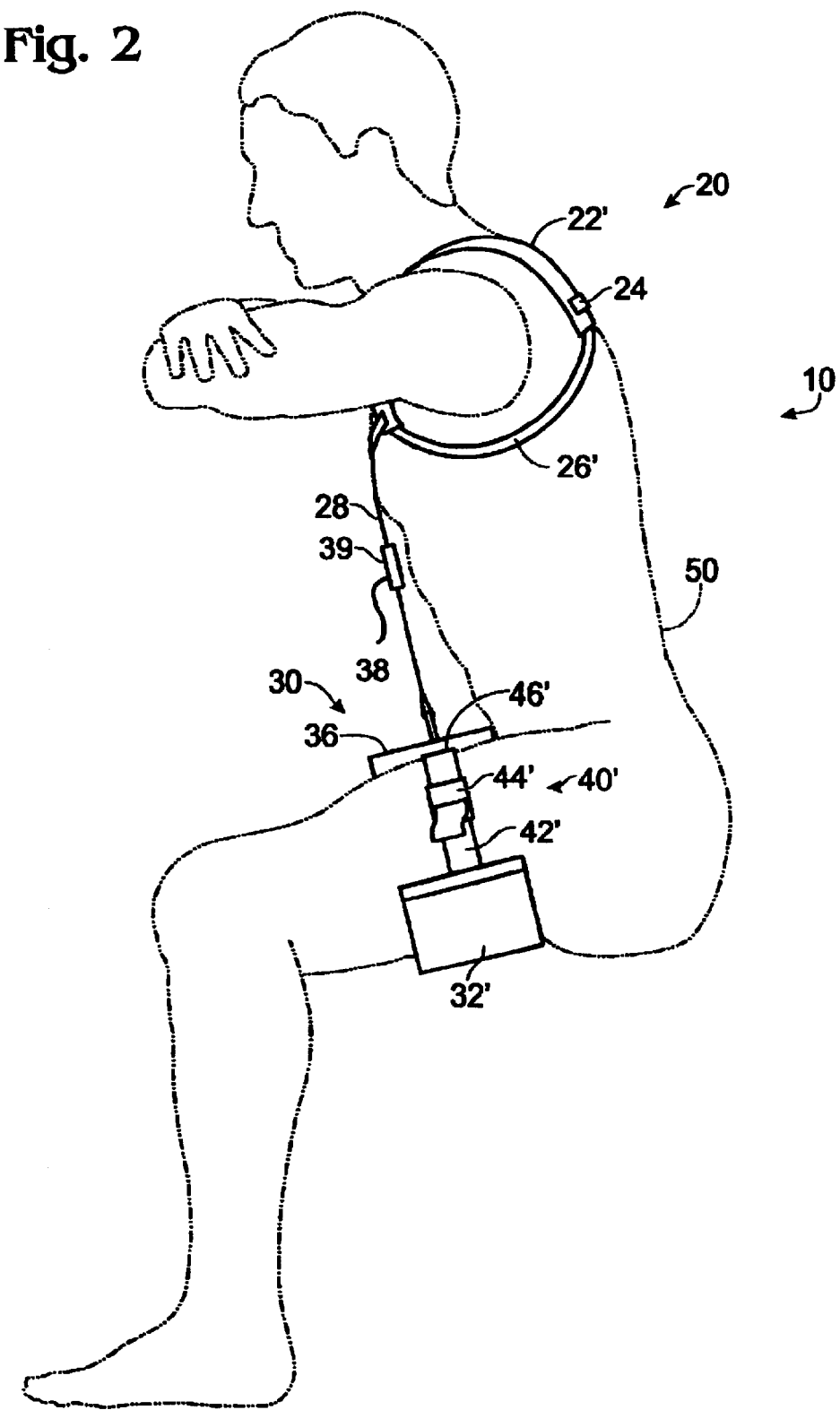
FIG. 2 is a left side view of the epidural positioning device of the present invention in place on a patient shown in phantom.

FIGS. 1 and 2 show the epidural positioning device 10 in place on a patient 50 (shown in phantom) to position the patient on his/her side in the fetal position.

In use, the patient 50 slips his/her right arm through the opening formed between shoulder hanger 22 and arm strap 26, and slips his/her left arm through the opening formed between shoulder hanger 22' and arm strap 26', while inserting his/her head through the opening formed between the outer, joined ends of straps 26 and 26' and rear cross member 24. Upon completion, shoulder harness subassembly is in the position on patient 50 shown in FIGS. 1 and 2.

Where arm straps 26 and 26' are omitted, the shoulder harness subassembly is simply placed over the head of the patient 50.

The leg saddle subassembly 30 is then positioned so that the area of the right and rear legs of patient 50 located just above and behind the patient's knees rests on right and left leg stirrup portions 32 and 32', respectively. Leg straps 40, 40' may be used to help secure the patient's legs to the leg saddle subassembly 30. The patient's legs are curled into the fetal position and chest strap 28 inserted into and through buckle 39. Chest strap 28 is tightened to restrain the patient 50 in the desired fetal position, and buckle 39 then holds chest strap 28 in that desired position throughout the lateral epidural procedure.

Upon completion of the lateral epidural procedure, buckle 39 is loosened to allow chest strap 28 to be removed, and the shoulder harness subassembly 20 and leg saddle subassembly 30 removed.

While buckle 39 is shown as being attached to strap 38 of leg saddle subassembly 30, it could be attached to chest strap 28 of the shoulder harness subassembly 30.

The word "buckle" as used herein is intended to include any conventional adjustable strap attachment means.

It will be obvious to those having skill in the art that many changes may be made to the details of the above-described embodiments of this invention without departing from the underlying principles thereof. The scope of the present invention should, therefore, be determined only by the following claims.

The invention claimed is:

1. A positioning device for a patient undergoing a lateral epidural procedure, said positioning device comprising:
- a shoulder harness subassembly having right and left shoulder hangers adapted to fit over the right and left shoulders, respectively, of said patient, said subassembly having a chest strap extending downwardly from the front thereof;
- a generally inverted U-shaped leg saddle subassembly having right and left legs extending downwardly from an upper juncture thereof, and right and left stirrup portions extending outwardly from the lower ends of said right and left legs, respectively, said right and left stirrup portions adapted to fit behind the legs of said patient, said saddle subassembly having a saddle strap extending upwardly from said juncture of said right and left legs thereof; and
- an adjustable strap attachment means attached to one of the lower end of said chest strap or the upper end of said saddle strap, said adjustable strap attachment means adapted to receive the other of said chest strap or saddle strap and hold said other strap in position.

* * * * *